United States Patent [19]

Krauss

[11] Patent Number: 5,385,058
[45] Date of Patent: Jan. 31, 1995

[54] METHOD AND APPARATUS FOR SAMPLING PARTICULATE MATERIAL FALLING FROM A BELT CONVEYOR

[75] Inventor: Kenneth J. Krauss, North Olmsted, Ohio

[73] Assignee: General Signal Corporation, Stamford, Conn.

[21] Appl. No.: 941,585

[22] Filed: Sep. 8, 1992

[51] Int. Cl.⁶ .............................. G01F 1/20; G01F 1/66
[52] U.S. Cl. .............................. 73/864.32; 73/864.31; 73/863.54
[58] Field of Search ........... 73/863.53, 863.54, 863.56, 73/864.31, 864.32

[56] References Cited

U.S. PATENT DOCUMENTS

| | | | |
|---|---|---|---|
| 1,223,544 | 4/1917 | Wendell | 73/864.32 |
| 2,495,944 | 1/1950 | Pletta et al. | |
| 2,664,751 | 1/1954 | Johnson | 73/864.31 |
| 3,187,944 | 6/1965 | Stock | |
| 3,791,218 | 2/1974 | Pennington | 73/863.54 |
| 4,326,425 | 4/1982 | Gunderson et al. | |
| 4,433,587 | 2/1984 | Risdal | |
| 4,518,699 | 5/1985 | Bohl | |
| 4,587,858 | 5/1986 | Bartholomay | |
| 4,631,968 | 12/1986 | Aske | 73/864.32 |
| 4,771,642 | 9/1988 | Parth et al. | |
| 4,790,196 | 12/1988 | Gould | 73/864.32 |
| 4,796,476 | 1/1989 | Long | 73/864.32 |
| 4,934,200 | 6/1990 | Lantz | |
| 5,072,624 | 12/1991 | Montgomery | |

OTHER PUBLICATIONS

Birtley Eng. Inc. product literature bulletin "The Birtley Automatic Sampling System for Onstream Bulk Mat'l Sampling" 5 pgs.
Gustafson "Automatic Sampling Systems" literature 3 pgs.
Neundorfer Engineered Equip. (Feb. 20, 1990) Sampler ENPA 0290 6 pgs.
Stock Tech Brief (Apr. 1, 1991) 3 pgs.
"Automatic Industrrial Systems"—InterSystems Samplers 3 pgs.
James A. Redding Co. Brochure.
Galigher Engineered Sampling Systems—Ramsey Eng. Co. 4 pgs. product literature.
Denver Equipment Div. product literature—3 pgs.
Mitsubishi Nagasaki Machinery Mfg. Co. Sampling Systems product literature—4 pgs.
Stock Equipment Co. brochure, product descriptions 14 pgs.

Primary Examiner—Richard E. Chilcot, Jr.
Assistant Examiner—William L. Oen
Attorney, Agent, or Firm—M. LuKacher

[57] ABSTRACT

A sampler having a pneumatically actuated scoop closes an opening in the bottom of a pipe containing an auger. The scoop swings through particulate material, (especially granular and/or powdered coal) as it is discharged from a belt of a feeder at the transition between where the coal is carried on the belt and where it falls over the end pulley around which the belt is entrained. The scoop extends across the full width of the belt and captures a sample of the material in the pipe where it is delivered by the auger to a discharge port. A valve connected to the discharge port maintains the pressure integrity of the feeder (at pressure above atmospheric pressure).

20 Claims, 4 Drawing Sheets

METHOD AND APPARATUS FOR SAMPLING PARTICULATE MATERIAL FALLING FROM A BELT CONVEYOR

DESCRIPTION

The present invention relates to methods and apparatus for sampling particulate material, by which is meant powders, beads, granules and the like and particularly to methods and apparatus for the automatic sampling of such materials in a stream which moves along and falls off a conveyor.

The invention is especially suitable for use in sampling coal of particle size such as used in electric power generating stations and particularly while the coal is transported in a gravimetric feeder which may be pressurized above atmospheric pressure for dust control and safety (explosion prevention) purposes.

The goal of particle sampling systems is to enable sampling while the material is being conveyed with an accuracy and precision approaching sampling when the material is stopped, it being undesirable, for example, to stop a belt carrying the material to take a sample.

It is undesirable to take a partial sample of a stream of material, for example, to less than over the entire cross section of the material in the stream. Then a bias or non-representative sample may be taken.

Sampling within the confines of a feeder, such as a coal feeder, is difficult because of the limitations in space in the enclosure of the feeder, especially where the feeder and the coal sample handling apparatus is pressurized, since the pressure integrity of the enclosure may be breached. Coal feeders of the type wherein a sampler is desirably incorporated are shown in U.S. Pat. No. 3,187,944, issued Jun. 8, 1965 to Arthur J. Stock. Accuracy of sampling is particularly important in coal being fed to the burners in electrical power generating plants, since the heat capacity and ash and contaminant content of the coal is determinative of the volume of coal required to meet the power generating needs of the station and to implement necessary ash and contaminant removal operations.

It is therefore a principal object of the present invention to provide an improved method of, and apparatus for, sampling particulate material, which are especially adapted for sampling coal which is used as fuel which is being fired (as-fired fuel) in power generating stations.

It is another object of the invention to provide an improved method of and apparatus for sampling of particulate material as it is being conveyed on a feeder, such as a gravimetric feeder used in conveying as-fired fuel to the burners in a power generating station.

It is a further object of the present invention to provide an improved method of and apparatus for sampling particulate material in a pressurized, explosion confining enclosure which avoids breaching the pressure integrity of the enclosure.

It is a still further object of the present invention to provide an improved method of and apparatus for sampling of particulate material accurately and precisely from a stream of the material as it is being fed and without having to stop the feeding of the material for the purpose of taking a sample.

It is a still further object of the present invention to provide an improved method of and apparatus for sampling of particulate material, particularly pulverized coal which accommodates variations in the rate at which the material is being fed.

It is a still further object of the present invention to provide an improved method of and apparatus for sampling of particulate material, especially pulverized coal, which is fail-safe in operation.

It is a still further object of the present invention to provide an improved method of and apparatus for sampling of particulate material which may be implemented in a restricted space and at lower cost than is the case for samplers which operate in sampling towers through which the material being sampled falls.

Briefly described, the invention is operative to sample predetermined quantities of particulate material, especially pulverized coal by capturing a sample quantity of the material in a scoop. The scoop contains a volume of material corresponding to the quantity and may extend across a stream of the material which is carried on a conveyor belt, such as the endless belts used in gravimetric feeders of the type described in the above-referenced Stock Patent. The scoop captures the precise quantity in a region defined by a closed bottom and an open top of the scoop. The scoop is articulated so that it travels downwardly along a path which passes the scoop's closed bottom through a flowing stream of the material toward a lower end of the path through a region of the path where the top of the scoop faces downwardly so that any material remaining in the scoop can fall out of the scoop before a new sample quantity is taken. Then the scoop is moved upwardly along the path through the flowing stream. The scoop moves to a position where it closes an opening in a channel or pipe which contains a conveyor, such as an auger, which moves the sample to a discharge port, which may be located at the end of the pipe. The path of the scoop may be arcuate and tangent to the belt where it passes around an end pulley of the belt conveyor. This is a transition point between where the material is on the belt and where it falls off the belt to form a waterfall-like stream of the particulate material.

The foregoing and other objects features and advantages of the invention, as well as a presently preferred embodiment thereof, will become more apparent from a reading of the following description in connection with the accompanying drawings in which.

Figure 1:
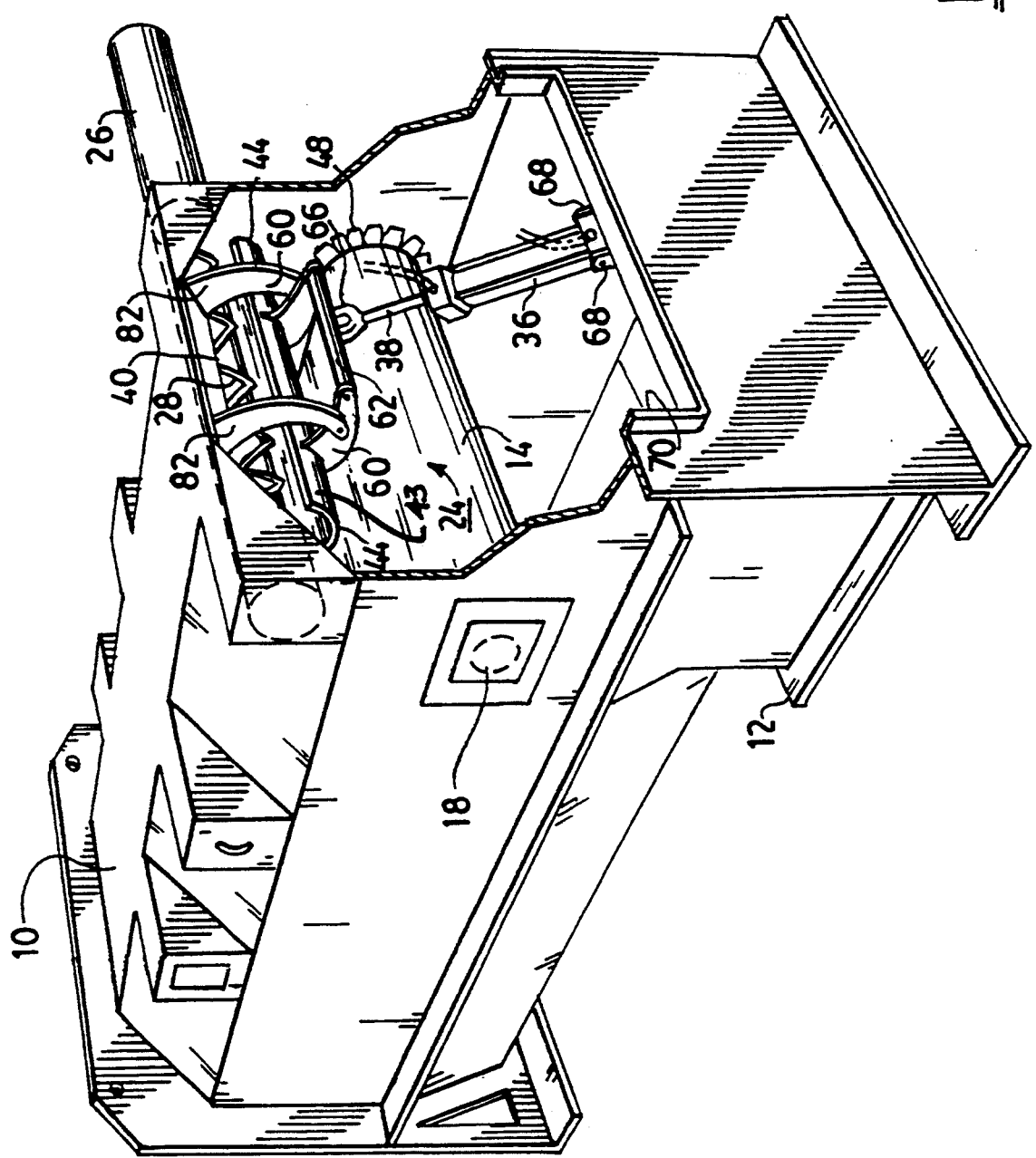
FIG. 1 is a perspective view of a sampler embodying the invention contained in the enclosure of a gravimetric feeder, the enclosure being broken away to illustrate the sampler.

Referring to FIG. 1, there is shown a particulate feeder designed for feeding granular and/or powdered coal. This feeder is a gravimetric feeder of the type described in the above-identified Stock Patent. Coal arrives at the feeder through a chute which may be disposed on the top or at the rear of the feeder body 10. The coal inlet chute is not shown to simplify the illustration. Coal also leaves through a chute connected to the bottom of the conveyor near the front end thereof. This chute is not shown, but may be connected to a flange 12 along the bottom of the conveyor body 10. The body is substantially airtight and is designed to be internally pressurized by compressed air from a compressor or blower. The internal pressure in the feeder enclosure may be as high as 3 psi (pounds per square inch), but is normally about 1.5 psi.

Internally of the conveyor is an endless feeder belt 14 which is entrained around an end pulley 16 mounted on a shaft rotatable in journals 18 on the side walls of the body 10. (See also FIGS. 2 and 4). The coal particles are carried on the belt in a layer which extends laterally across the width of the belt 14. A stream 20 (see FIG. 4) of coal reaches an effective ledge in a sector 22 defined by horizontal and vertical diameters 25 and 27 of the end pulley 16 and falls over this ledge downwardly to the collection chute at the bottom of the feeder body. The transition zone between where the coal is fed on the belt and where it falls downwardly from the belt is in this sector 22. In this sector, the thickness of the coal is well defined. Normally, the thickness of the coal is about 2 inches above the surface of the belt. The layer of coal extends essentially the entire width of the belt. After the transition, the thickness of the stream is not well defined. Such that sampling in such a region may produce imprecise results, which is known as a bias sample.

Also contained in the coal feeder body below the feeder belt 14 is a clear out conveyor, (not shown), made up of bars carried on endless chains on sprockets. The shaft through these sprockets is rotatable in journals 22 below the journals 18 (FIG. 3).

The feeder as described is used in electrical generating power stations. It is a feature of this invention to incorporate a sampler 24. This sampler, as shown in FIG. 1, is within the feeder body and is internally pressurized with the other components of the feeder. The sampler has a sample delivery channel provided by a cylindrical pipe 26 containing a sample transporting conveyor in the form of an auger or screw conveyor 28 internally thereof. The pipe 26 extends through a side wall of the body 10.

Figure 2:
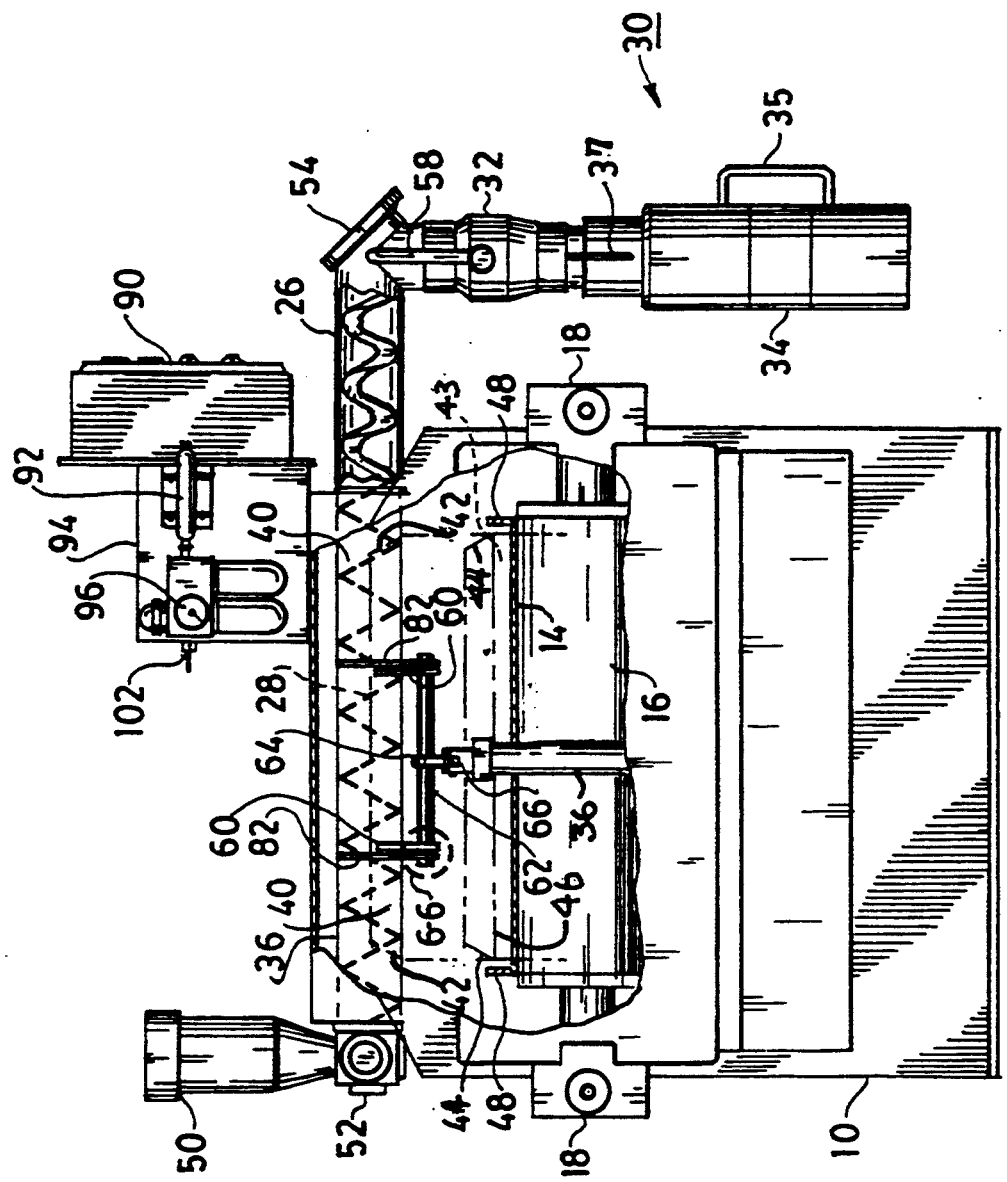
FIG. 2 is an end view of the apparatus shown in FIG. 1, which is partially broken away to illustrate the sampler.
Figure 3:
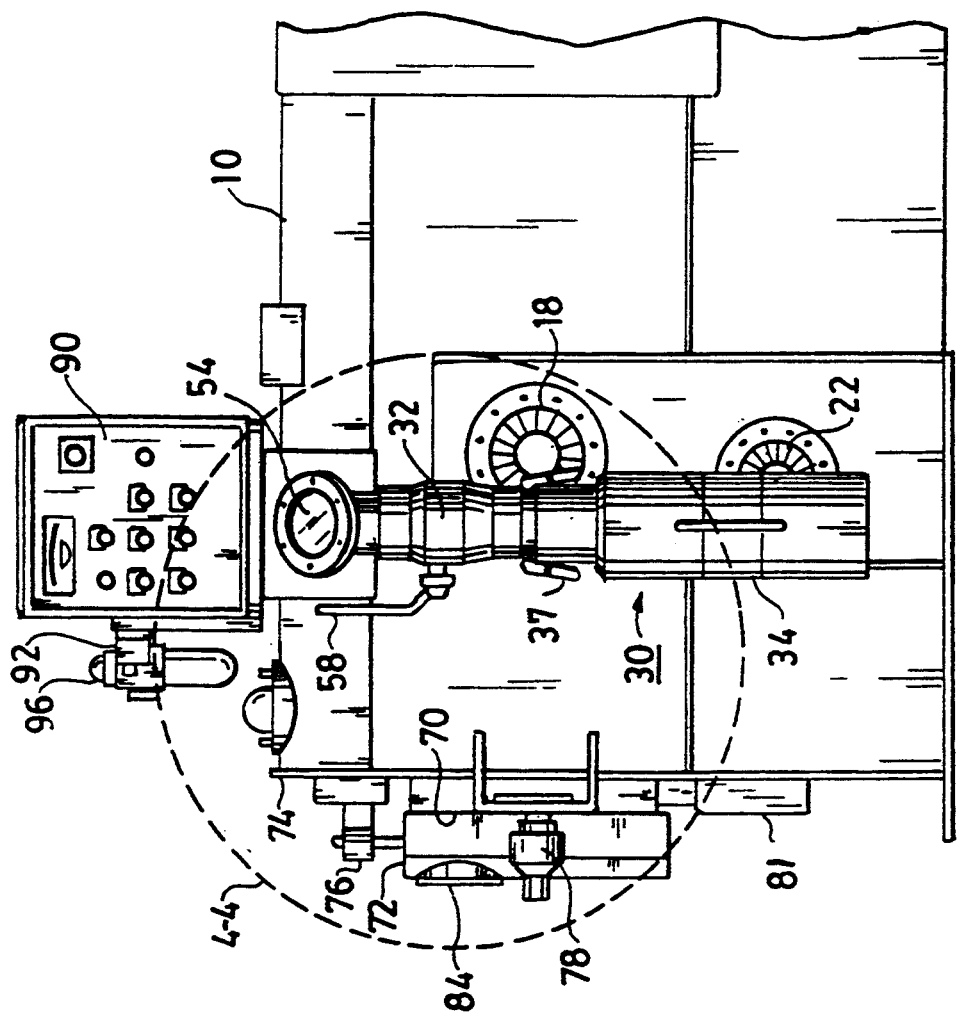
FIG. 3 is a fragmentary, side elevation of the sampler shown in FIGS. 1 and 2.

The sample is delivered to and collected in a collection unit 30 (as shown in FIGS. 2 and 3, but not in FIG. 1). This collection unit has a valve 32 which maintains the internal pressure in the enclosure 10, except at such times when sample collection is carried out or a pressure resistant sample container 34 is connected. The sample container 34 is attached by a quick disconnect fitting 27 to the outlet of the valve 32. Instead of a single valve, a pair of valves may be provided which establish between them an air lock. Then after a sample is delivered through the upper one of the valves, it is closed and the lower valve opens, so as to deliver the sample to a bucket or a conveyor leading to an analyzing station. Such analyzing stations may be similar to those which have heretofore been used for sample collection and analysis.

The internal pressurization of the sampler 24 and the components of the feeder is, under either automatic or manual collection operation, maintained. Such pressurization is provided for safety purposes. All components within the enclosure which are subject to pressure in pulverized coal systems, pursuant to applicable safety standards are designed to withstand 50 psi explosion pressure. This is the case with the feeder and the components of the sampler which are subject to pressure and coal particles or dust. For example, the container 34 is desirably designed to withstand 50 psi explosion pressure. The collection pipe 26 and other components of the sampler 24 are sufficiently of a small size to be contained within the feeder body 10. It may be desirable, for example, in the interest of ease of maintenance, to locate some parts of the sampler, particularly a pneumatic cylinder 36 thereof, outside of the containment in the body 10. Then a seal may be provided in the enclosure body 10, through which a reciprocal rod 38 of the pneumatic cylinder actuator 36 passes, so as to maintain the pressure integrity of the feeder body.

The sampler 24 collects samples in a scoop 43. The scoop 43 is shown as it leaves or arrives from an end position on its path in FIG. 1. This view exposes an opening 40 in the pipe 26, which is generally hemi-cylindrical, but may have outwardly tapered ends 42 when the ends 44 of the scoop taper outwardly. The scoop, extends as shown in FIG. 2 by the dash lines 46 where the scoop is adjacent to the belt 14, laterally a width approximately equal to the width of the belt 14 in the lateral direction. Guards 48 made up of segments extend upwardly along the lateral edges of the belt 14 and restrict the layer of particles to the belt. The width of the scoop is approximately equal to the lateral distance between the guards 48. Thus, the scoop samples the particulate material (coal or limestone particles or powder in power-generating applications) where it lies across the width of the belt 14.

The scoop 43 is hemi-cylindrical and the opening 40 is generally hemi-cylindrical. Accordingly, at the upper end of its path, the scoop is disposed in closing relationship with the pipe 26. The auger 28 is driven by a drive motor 50 operating through a gear box 52 to turn the auger in a direction which moves the collected sample through the pipe 28 where it drops into the collection unit 30. A view port 54 at the junction of the collection unit and the pipe 26 allows the operator to observe the motion of the auger and the movement of the coal into the collection unit 30 (see FIGS. 2 and 3).

Figure 4:
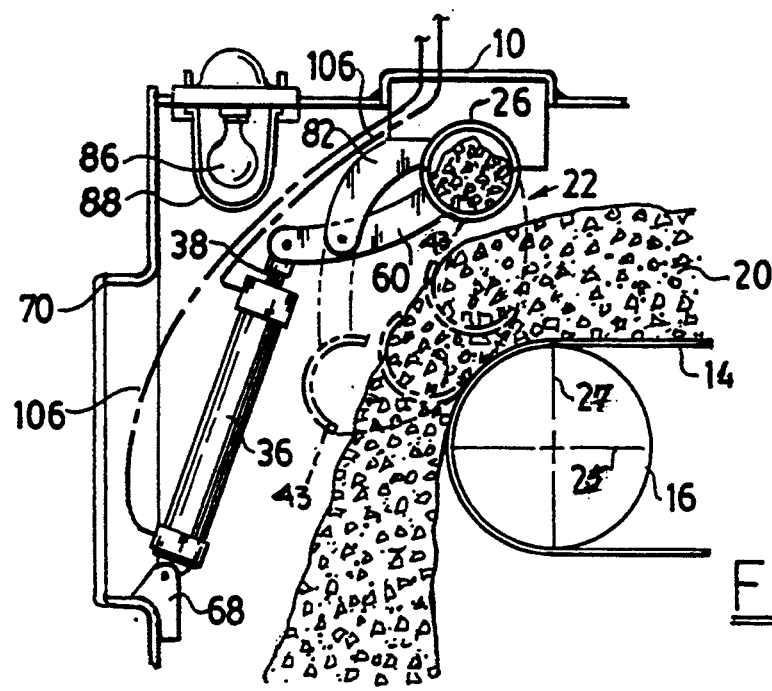
FIG. 4 is an enlarged, sectional view of the sampler taken in the region enclosed by the circle 4—4 in FIG. 3.

The valve 32 of the collection unit 30 is manually operated by a control lever 58. The valve may be operated automatically by a valve actuator motor, which is electrically operated. The electrical control system controls the application of compressed air to the cylinder 36 and also controls the motor 50; preferably starting the motor 50 to drive the auger before movement of the scoop 36 through the material as it falls from the belt in the transition zone 22 (FIG. 4).

The auger operates continuously as the coal is advanced into the pipe 26 and the scoop remains in its upper position, closing the pipe until the sample is passed through the pipe for collection. A complete sample purge is accomplished at the end of each sample collection cycle.

The sampler 24 also includes a pair of arms 60, which are connected to a cross arm 62, to which a stub 64 is welded at the center thereof. This stub is pivotally connected to a yoke 66 at the end of the piston rod 38. The opposite end of the cylinder 36 is pivotally connected to brackets 68 which are welded to the enclosure 10 at an opening 70 (see FIGS. 1 and 3) for a door 72 which is hinged to the forward end 74 of the enclosure 10 at a hinge mechanism 76. The door is closed and locked in sealed relationship with the opening 70 by a bolt mechanism 78. The frame which forms the opening 70 may be stiffened by a strut 81 where the brackets 68 are located.

Figure 6:
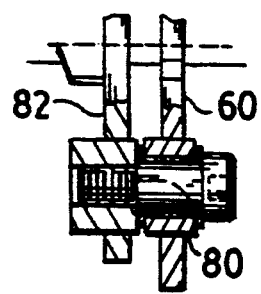
FIG. 6 is an enlarged view showing the pivotal connection between the cylinder and the scoop of the feeder, the view being taken in the region indicated by the circular line 6—6 in FIG. 2.

The arms 60 are connected by a pivot joint 80 to support brackets or arms 82 (see also FIG. 6), which are welded to the outside of the pipe 26.

As shown in FIG. 4, the arms 60 and the cylinder 36 provide an articulated connection to the scoop 36, which causes the scoop to execute a generally circular, arcuate path through the transition zone in sector 22. At the beginning of a cycle, the scoop is moved along the path from the upper end thereof where the scoop is in closing relationship with the pipe 26 to the lower end thereof, where the scoop may be stopped against the cylinder 36. The scoop moves through the material 20 to a position where it clears the fall of the material off the belt 14 at the end pulley 16. In clearing the fall, the scoop passes vertical so that the open top of the scoop faces downwardly at, or just before, reaching the lower end of its travel, and any material remaining in the scoop on the last cycle can drop out of the scoop, thereby providing an empty scoop for collection of the next sample.

The path of the scoop 38 (See FIG. 4) is tangent to the belt in the sector 22 around the end pulley 16, thereby assuring a collection of the entire depth or thickness of the layer of material 20 as the scoop makes a sample collection pass in the upward direction.

The collection operation may be viewed through a viewing port 84, and the door 72 under the illumination from a lamp 86 which is located in a pressure resistant, transparent guard 88, see FIGS. 3 and 4. After a collection cycle, the sample will be contained in the container 34. Then the valve 32 is closed by operating the handle 58 and the container 34 is released and may be carried by its handle 35 for weighing and other analysis of the sample.

Figure 5:
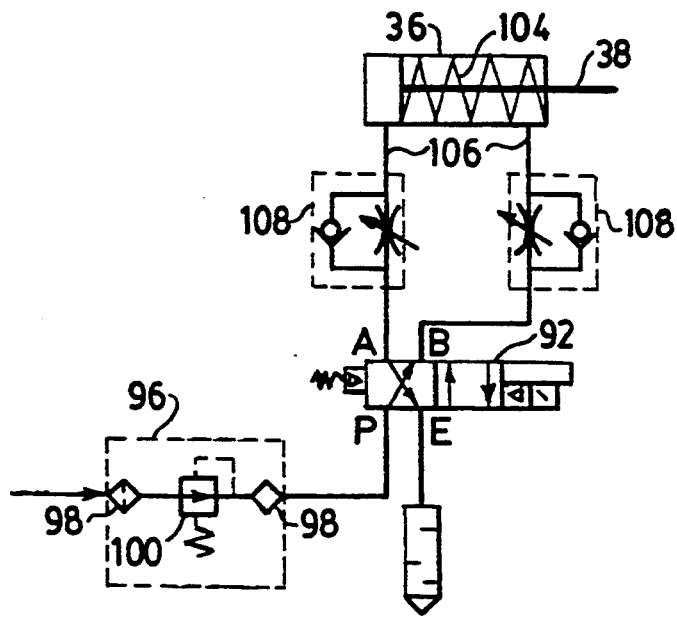
FIG. 5 is a schematic diagram of the pneumatic circuit for operating the cylinder which operates as an actuator in the sampler illustrated in the preceding figures.

The electrical control circuits and push buttons for the sampler are mounted on and contained in a control panel 90 (FIGS. 2 and 3). The pneumatic circuit of the system is shown in FIG. 5. It includes a control valve 92 which is mounted on a panel 94 attached to the top of the enclosure 10. A filter, regulator and lubricator assembly 96, having filters 98 and a control valve 100, is located at the inlet for pressurized air from a compressor or other compressed air supply, which is connected to a nipple 102 (see FIG. 2).

The cylinder 36 has a spring 104, which causes the piston rod 38 to move inwardly, bringing the scoop 36 to its upper end position in closing relationship with the pipe 26. Air supply hoses 106 (see also FIG. 4) extend through check valve and variable orifice assemblies 108 to the valve 92. The valve is solenoid-actuated by the electrical control circuit of the system. Pressurized air is applied to the cylinder to retract the rod 38 in the position shown in FIG. 5. When the valve 92 is actuated, it switches position and applies pressurized air, first extending the rod so that the scoop is brought to its lower end position. The scoop can then remain at that position for a fixed period of time as determined by a time delay circuit in the electrical controller which operates the solenoid of the valve 92. Then the valve is actuated, and air is applied to actuate the cylinder 36 and moves the scoop through the coal along the arcuate path as illustrated in FIG. 4. The scoop is maintained in closing relationship with the pipe 26 until the scoop conveyor or auger 38, which was started prior to the beginning of the cycle, and which continues to turn causes the pipe to be purged and the sample to be collected. The cycle may be started manually or repeated at preset time intervals (automatically).

The rate at which the scoop moves through the coal stream 20 is controllable by varying the pressure with the variable orifices in the orifice, check valve assemblies 108. Accordingly the scoop closing rate may be adjusted to accommodate the speed of the belt. This adjustable scoop closing rate allows sample collection at low feed rates (e.g., below ten tons per hour) in a typical coal feeder.

From the foregoing description it will be apparent that there has been provided an improved method of and apparatus for sampling of particulate material, especially particulate or granular coal, limestone or the like. Variations and modifications in the herein described method and apparatus, within the scope of the invention, will undoubtedly suggest themselves to those skilled in the art. Accordingly, the foregoing description should be taken as illustrative, and not in a limiting sense.

I claim:

1. A method for sampling particulate material which is flowing in a downwardly falling stream through a transition zone at the upper end of the downwardly falling stream to which the material is carried by a belt, and delivering said material to a fixed delivery channel having a downwardly facing opening through which the material can fall unless said opening is closed, which method comprises the steps of moving a scoop having a closed bottom and an open top through the transition zone of said stream with the bottom of said scoop facing downwardly and without receiving material in said scoop while so moving downwardly to a position clear of said stream where the open end of said scoop faces generally downwardly, then moving said scoop upwardly through said transition zone of said stream with said top facing upwardly to pick up a sample of said material, and delivering said material to said channel with said scoop closing said opening when said delivering step is being carried out.

2. The method according to claim 1 wherein said downwardly and upwardly moving steps are carried out by moving said scoop along an arcuate path.

3. The method according to claim 2 wherein said steps of moving said scoop is carried out by swinging said scoop in opposite directions along said path.

4. The method according to claim 1 further comprising the step of moving said material to a ledge which defines said transition zone and over which said material falls in said downwardly falling stream.

5. The method according to claim 4 wherein said ledge is defined by a pulley at the end of an endless belt conveyor which carries out said step of moving said material, and said path is tangent to said pulley where said falling stream begins.

6. The method according to claim 1 wherein said delivery channel leads to a collection point and wherein said stream of material, said scoop and said channel are in an enclosure which is pressurized above atmospheric pressure, and closing said channel with a valve which is opened to enable to said sample to be transported to said collection point, while maintaining said enclosure pressurized 7. Apparatus for sampling a predetermined quantity of particulate material which flows in a stream, which apparatus comprises a scoop, having a perimeter which defines an area, movable along a path, having spaced ends, through the stream for collecting said quantity upon passing between one of said spaced ends of said path to another of said spaced ends of said path, and a stationary sample delivery channel having an opening, which is not capable of retaining said material while open and of at least said area, and which receives said scoop therein in closing relationship with said channel over said opening when said scoop reaches said another of said opposite ends of said path and thereby provides means for locating said sample in sample delivering position in said channel.

8. The apparatus according to claim 7 further wherein said channel has an outlet, and further comprises particulate conveying means in said chute for delivering said sample to said outlet.

9. The apparatus according to claim 8 wherein said channel is defined by a wall of a pipe, with an open section defining said opening, said scoop having a shape conforming to the shape of said wall and closing said open section when said scoop is deposed in said closing relationship.

10. The apparatus according to claim 9 further comprising an auger in said pipe for moving said sample to discharge opening in said pipe.

11. The apparatus according to claim 7 further comprising an enclosure pressurized above atmospheric pressure, conveying means in said enclosure for providing said stream of said material, said channel and said scoop also being disposed in said enclosure said channel having a discharge port external of said enclosure, and valve means external to said enclosure for maintaining said discharge and said enclosure sealed.

12. The apparatus according to claim 7 further comprising an arm on which said scoop is mounted, and said arm being pivotally mounted for movement along an arcuate path between said spaced ends at said another of which said scoop is disposed in said closing relationship with said channel and at said one of which said scoop is spaced from said stream.

13. The apparatus according to claim 12 wherein said another end is above said one end and said another and one of said spaced ends defined upper and lower ends of said path, respectively, said scoop having an open top and a closed bottom, and means for moving said scoop so that said top is facing generally downwardly at or near said lower end of said path to enable material in said scoop to empty therefrom at or adjacent to said lower end.

14. The apparatus according to claim 12 further comprising at least one arm on which said scoop is mounted, said arm being pivotally mounted, and an actuator connected to said arm to pivot it and reciprocate said scoop between the ends of said path.

15. The apparatus according to claim 14 wherein said actuator is a cylinder with a reciprocable rod which is pivotally connected to said arm.

16. The apparatus according to claim 14 further comprising at least one strut connected to said channel, said arm having opposite ends and being pivotally connected to said strut intermediate the ends thereof, one of the opposite ends of said arm having said scoop attached thereto, and the other of said opposite ends of said arm being pivotally connected to a piston rod of a cylinder which provides said actuator.

17. The apparatus according to claim 16 wherein said channel is a cylindrical pipe having means therein for conveying said sample towards a discharge port, said opening being generally hemi-cylindrical said scoop being generally hemi-cylindrical and having an open top which faces upwardly to conform to said opening when in said closing relationship at the upper end of said path and is tipped downwardly when at the lower end of said path to enable material contained in said scoop to fall out of said scoop.

18. In a feeder for particulate material having an endless belt on which said material is conveyed towards an end pulley on which said belt is entrained defining a ledge over which said material falls in a descending stream, apparatus for sampling and providing a sample of a predetermined quantity of said material which comprises a scoop movable along a path through the stream for collecting said sample and sample delivery channel means having an opening for receiving said scoop therein in closing relationship with said channel and with said sample in sample delivering position in said channel.

19. The apparatus according to claim 18 further comprising an arm on said scoop mounted for movement along an arcuate path through said stream within a sector defined by horizontal and vertical lines extending outwardly from said belt.

20. The apparatus according to claim 18 wherein said scoop extends laterally in a direction across said belt and has a width approximately equal to the width of said belt on which said material is disposed.

* * * * *